United States Patent
Bilen-Rosas et al.

(10) Patent No.: US 11,819,321 B2
(45) Date of Patent: Nov. 21, 2023

(54) SYSTEM AND METHOD FOR MONITORING AIRFLOW IN A SUBJECT'S AIRWAY WITH ULTRASOUND

(71) Applicant: Wisconsin Alumni Research Foundation, Madison, WI (US)

(72) Inventors: Guelay Bilen-Rosas, Middleton, WI (US); Humberto Gerardo Rosas, Middleton, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 339 days.

(21) Appl. No.: 16/272,689

(22) Filed: Feb. 11, 2019

(65) Prior Publication Data

US 2019/0167227 A1    Jun. 6, 2019

Related U.S. Application Data

(63) Continuation-in-part of application No. PCT/US2017/052233, filed on Sep. 19, 2017.

(Continued)

(51) Int. Cl.
*A61B 5/087* (2006.01)
*A61B 8/00* (2006.01)
(Continued)

(52) U.S. Cl.
CPC ............ *A61B 5/087* (2013.01); *A61B 5/7267* (2013.01); *A61B 5/742* (2013.01); *A61B 5/7405* (2013.01);
(Continued)

(58) Field of Classification Search
CPC ..... A61B 5/087; A61B 5/7267; A61B 5/7405; A61B 5/742; A61B 5/746; A61B 8/08;
(Continued)

(56) References Cited

U.S. PATENT DOCUMENTS 6,537,228 B1    3/2003    Lambert
7,116,810 B2   10/2006    Miller et al.
(Continued)

FOREIGN PATENT DOCUMENTS

AU    2004222800 A1    11/2004
CN    100528078 C      8/2009
(Continued)

OTHER PUBLICATIONS

Palti, Yoram, et al. "Pulmonary Doppler signals: a potentially new diagnostic tool." European Journal of Echocardiography 12.12 ( 2011): 940-944. (Year: 2011).*

(Continued)

*Primary Examiner* — Joel Lamprecht
*Assistant Examiner* — Ashish S Jasani
(74) *Attorney, Agent, or Firm* — Quarles & Brady, LLP (57) ABSTRACT

Described here are systems and methods for monitoring airflow changes in a patient's airway during a medical procedure or as a general patient monitoring tool. Doppler ultrasound signals are acquired from an anatomical region within the patient's airway (e.g., a tracheal wall, a cricothyroid ligament, other connective or cartilaginous tissue within the trachea, larynx, or pharynx) and parameters from those Doppler ultrasound signals are compared to baseline parameters, which may include inputting Doppler ultrasound signals to a suitably trained deep learning model or other machine learning algorithm. When a threshold change is detected, an alarm can be provided to a user to indicate respiratory compromise and/or failure, which can include early airway compromise, airway failure, and/or airway obstruction.

24 Claims, 8 Drawing Sheets

Related U.S. Application Data (60) Provisional application No. 62/396,339, filed on Sep. 19, 2016.

(51) Int. Cl.
    *A61B 8/08*     (2006.01)
    *A61B 5/00*     (2006.01)
    A61B 5/085     (2006.01)
    A61B 5/08     (2006.01)
    A61B 7/00     (2006.01)

(52) U.S. Cl.
    CPC ............... *A61B 5/746* (2013.01); *A61B 8/08* (2013.01); *A61B 8/469* (2013.01); *A61B 8/488* (2013.01); *A61B 5/085* (2013.01); *A61B 5/0816* (2013.01); *A61B 5/4821* (2013.01); *A61B 7/003* (2013.01)

(58) Field of Classification Search
    CPC ......... A61B 8/469; A61B 8/488; A61B 7/003; A61B 5/4821; A61B 5/085; A61B 5/0816; A61B 8/5207
    See application file for complete search history.

(56) References Cited

U.S. PATENT DOCUMENTS

| | | | |
|---|---|---|---|
| 2006/0081255 A1* | 4/2006 | Miller ................ | A61M 16/04 128/207.14 |
| 2011/0273299 A1 | 11/2011 | Milne et al. | |
| 2013/0289401 A1 | 10/2013 | Colbaugh et al. | |
| 2014/0039313 A1* | 2/2014 | Palti ................... | A61B 8/5223 600/438 |
| 2015/0164433 A1* | 6/2015 | Halperin ............. | A61N 1/3956 600/529 |
| 2015/0209001 A1* | 7/2015 | Wolf ................... | A61B 8/15 600/301 |
| 2015/0216509 A1 | 8/2015 | Yamagata et al. | |
| 2015/0316520 A1 | 11/2015 | Maguire et al. | |

FOREIGN PATENT DOCUMENTS

| | | |
|---|---|---|
| CN | 201445694 U | 5/2010 |
| CN | 103417184 A | 12/2013 |
| CN | 104254283 A | 4/2018 |
| WO | 2006/117780 A2 | 11/2006 |
| WO | 2015166485 A1 | 11/2015 |
| WO | 2015/179911 A1 | 12/2015 |

OTHER PUBLICATIONS

Arlotto, Philippe et al. "An ultrasonic contactless sensor for breathing monitoring." Sensors (Basel, Switzerland) vol. 14,8 15371-86. Aug. 20, 2014, doi:10.3390/s140815371 (Year: 2014).*

Vivier et al., "Diaphragm ultrasonography to estimate the work of breathing during non-invasive ventilation," (Apr. 5, 2012), Intensive Care Med (2012) 38:796-803. (Year: 2012).*

American Hospital Association The migration of care to non-hospital settings: have regulatory structures kept pace with changes in care delivery? TrendWatch, Jul. 2006. http://www.aha.org/research/reports/tw/twjuly2006migration.pdf.

Bae HK, et al. Cardiovascular screening in asymptomatic adolescents with metabolic syndrome. J Cardiovasc Ultrasound. 2015;23:10-19.

Barker, S. J., et al. (1997). The effects of motion on the performance of pulse oximeters in volunteers (revised publication). Anesthesiology, 86(1), 101.

Bhananker SM, Posner KL, Cheney FW, Caplan RA, Lee LA, Domino KB. Injury and liability associated with monitored anesthesia care: a closed claims analysis. Anesthesiology 2006; 104: 228-34.

Brunke SS, et al. An ultrasound research interface for a clinical system. IEEE Trans Ultrason Ferroelectr Freq Control. 2007;54(1):198-210.

Chapelon, J., et al. (2000). New piezoelectric transducers for therapeutic ultrasound. Ultrasound In Medicine & Biology, 26(1), 153-159. http://dx.doi.org/10.1016/s0301-5629(99)00120-9.

Cullen KA, et al. Ambulatory surgery in the United States, 2006. US Department of Health and Human Services, Centers for Disease Control and Prevention, National Center for Health Statistics; Jan. 28, 2009, Revised Sep. 2009.

Lee, Helen H., et al. "Trends in death associated with pediatric dental sedation and general anesthesia." Pediatric Anesthesia 23.8 (2013): 741-746.

Mackenzie et al. Are ambulatory surgical patients as healthy as we think? Using a self-reported health status questionnaire to identify unsuspected medical comorbidities. Hss J. 2006;2(2):121-6.

Mamie C, et al. Incidence and risk factors of perioperative respiratory adverse events in children undergoing elective surgery. Paediatr Anaesth. 2004;14(3):218-24.

Mason, K. P. "Challenges in paediatric procedural sedation: political, economic, and clinical aspects." British journal of anaesthesia 113.suppl_2 (2014): ii48-ii62.

Nagueh SF, et al. Doppler tissue imaging: A noninvasive technique for evaluation of left ventricular relaxation and estimation of filling pressures. Journal of the American College of Cardiology. 1997;30:1527-1533.

Nagueh SF, et al. Hemodynamic determinants of the mitral annulus diastolic velocities by tissue Doppler. Journal of the American College of Cardiology. 2001;37:278-285.

Sheahan CG, et al. Monitoring and delivery of sedation. British Journal of Anaesthesia 113 (S2):ii37-ii47, 2014.

Singh, M., et al. (2010). Use of sonography for airway assessment an observational study. Journal of Ultrasound in Medicine, 29(1), 79-85.

Sohn DW, et al. Assessment of mitral annulus velocity by Doppler tissue imaging in the evaluation of left ventricular diastolic function. Journal of the American College of Cardiology. 1997;30:474-480.

Urman RD, et al. Improving patient safety in the office: the Institute for Safety in Office-Based Surgery. APSF Newsl. 2011;26(1):3-4.

International Search Report and Written Opinion dated Dec. 11, 2017 from Parent Application PCT/US17/052233, 15 pages.

Kristensen, Ultrasonography in the Management of the Airway, Acta Anaesthesiologica Scandinavica, 2011, 55:1155-1173.

Philips, HD11 Xe Echocardiography System, Product Brochure, Copyright 2008 Koninklijke Philips Electronics N.V., 12 pages.

Reeder et al., Use of Doppler Techniques (Continuous-Wave, Pulsed-Wave, and Color Flow Imaging) in the Noninvasive Hemodynamic Assessment of Congenital Heart Disease, Mayo Clinic Proceedings, 1986, 61:725-744.

* cited by examiner

SYSTEM AND METHOD FOR MONITORING AIRFLOW IN A SUBJECT'S AIRWAY WITH ULTRASOUND

CROSS-REFERENCE TO RELATED APPLICATIONS

This application is a continuation-in-part of claims the benefit of International Application No. PCT/US2017/052233, filed on Sep. 19, 2017, which claims the benefit of U.S. Provisional Application No. 62/396,339, filed on Sep. 19, 2016, both of which are herein incorporated by reference in their entirety.

BACKGROUND

In the past few decades, advances in monitoring technology have contributed to a heightened sense of safety during medical procedures. Despite technological advancements and improved anesthetic agents leading to an increased safety profile of anesthesia and sedation, morbidity and mortality rates remain high in spontaneously breathing patients. One of the primary reasons morbidity and mortality rates remain high is the delayed detection of early respiratory compromise and/or failure, which impedes the timely implementation of rescue measures. Respiratory failure can occur within minutes to seconds, or it can develop gradually, both of which are difficult to predict. The end results of respiratory compromise and/or failure is insufficient oxygen to the brain and heart, leading to grave consequences including permanent neurological and cardiac damage, or even death. Currently available monitoring devices and techniques continue to be ineffective at alerting to subtle airflow changes in the early stages of respiratory compromise and/or failure.

Respiratory compromise and/or failure may include one or more of the following scenarios for respiratory activity: alterations in respiratory rate, decreased effort leading to decreased depth of breathing, obstruction in the upper airway anatomy (e.g., tongue obstruction, tissue obstruction, vocal cord spasms), or alterations in lower airway structures (e.g., bronchospasm, pneumonia). Patients under sedation can experience decreased respiratory effort, decreased respiratory rate, and varying degrees of tissue laxity, which can lead to airway obstruction and both of which are difficult to assess. Any combination of these mechanisms can lead to diminished airflow and/or changes in airflow, which prevents gas exchange for oxygen and carbon dioxide.

Because of the lack of reliable respiratory monitoring, early recognition of respiratory compromise and/or failure relies heavily on clinical expertise, and often using subjective clinical assessment and approximated evaluation of respiratory activity. Accurately monitoring for respiratory compromise and/or failure is especially difficult in pediatric patients, whose anatomy makes maintaining airway and respiratory homeostasis challenging during inhalation induction for anesthesia or sedation. The head and neck anatomy of pediatric patients, as well their unique respiratory physiology, predisposes this patient population to a higher incidence of airway obstruction and rapid rate of desaturation. For example, pediatric patients experience higher rates of tongue obstruction during sedation and anesthesia due to their larger tongue size in relation to their oral cavity. Additionally, at baseline, pediatric patients have two- to three-fold higher oxygen consumption; decreased functional capacity leading to diminished oxygen reserves once apneic; decreased type-1 muscle fibers resulting in faster respiratory fatigue during times of labor; and a closing capacity that is at the level of tidal volume breathing.

Any loss in the degree of respiratory effort brought about by sedation/anesthesia or respiratory illness will tip the balance from staying stable and ventilating appropriately to quick ventilatory compromise and/or failure, respiratory deterioration with decrease in airflow, and desaturation (i.e., type-2 respiratory failure). Unrecognized and delayed respiratory support requiring skilled airway maneuvers (e.g., hand-bag-ventilation) will lead to severe desaturation followed by bradycardia, which can be fatal for the patient.

As mentioned above, the currently available methods for monitoring respiratory compromise and/or failure are ineffective at directly measuring airflow changes in non-intubated patients and spontaneously breathing patients, thereby rendering the methods unreliable for accurately and timely detecting early respiratory compromise and/or failure.

One of the most common methods currently employed for monitoring airflow is measuring end-tidal carbon dioxide ("$CO_2$"). However, measuring end-tidal $CO_2$ has inherent limitations because it is an indirect measurement of alterations in airflow and becomes increasingly inaccurate in non-intubated patients due to the lack of a closed circuit. As a consequence, the measured data are difficult for the practitioner to interpret in spontaneously breathing patients, which often leads to delays in the treatment of early airway compromise and/or respiratory failure.

Another common method for monitoring for respiratory compromise and/or failure is pulse oximetry, which indirectly measures a patient's oxygen saturation and which is a standard American Society of Anesthesiologists ("ASA") monitor in operating rooms and most office-based sedation cases. However, pulse oximetry does not directly monitor respiration and hence does not monitor ventilation. For example, an obstructed airway will decrease oxygen flow and hence oxygen supply to the body, leading to desaturation (i.e., a drop in oxygen). The limitation of pulse oximetry is a delayed response to desaturation, resulting in a time lag in the detection of hypoxic events, particularly in the presence of supplemental oxygen.

Electrocardiography ("ECG") monitoring, a non-respiratory monitor, can also be used, but only shows changes in heart rate (e.g., bradycardia) once arterial oxygen desaturation has exceeded a critical point. Thus, like end-tidal $CO_2$ and pulse oximetry, ECG only indirectly measures respiratory compromise and/or failure by displaying changes in heart function (e.g., drop in blood pressure and heart rate) due to decreased oxygen supply to the heart as the consequence of airflow deterioration. Moreover, ECG-monitoring does not provide real-time measurements necessary to timely identify early airway compromise and/or failure.

Thoracic impedance monitoring can also be used for post-operative respiratory rate assessment. This measurement technique, however, is very susceptible to erroneous readings secondary to motion artifact. For instance, this methodology will continue to record a respiratory rate despite the patient breathing against a closed glottis, a situation in which airflow has ceased partially or completely.

Presently, the success of early detection of respiratory compromise and/or failure relies heavily on physician expertise. A non-invasive method of quantifying small changes in airflow patterns would allow physicians with various degrees of experience and in various circumstances to detect early respiratory compromise and/or failure, specifically in the outpatient setting where sedation is delivered by non-anesthesiologists; in the ICU where pain management, particularly with opioids, can lead to over-sedation; in the post-anesthesia recovery unit where patients are still awakening from anesthesia; in the emergency room where patients are presenting with respiratory issues due to trauma, reactive airway exacerbations, or infection; and in the operating room for inhalation and intravenous induction. In the setting of a mass casualty (e.g., in battlefield medicine or natural or human disasters) triage is very challenging. Yet, triage can be life-saving if respiratory compromise and/or failure is detected early and treated timely. Detecting not only progressively worsening respiratory problems (e.g., those due to infection, toxic exposure, allergens), but also indicating the cause (e.g., asthma attack versus tongue swelling) would be important and advantageous for clinicians.

Thus, there remains a need for a non-invasive system and method for directly and timely monitoring for respiratory compromise and/or failure, in addition to airflow changes in patients. Such a system would preferably not only detect respiratory issues, but also be able to indicate the underlying cause of respiratory compromise and/or failure (e.g., obstructive versus central apnea, or upper airway versus lower airway issues). Such a system and method would be advantageous not only for clinical and outpatient settings, but for research and teaching applications, too. Such a tool would objectively prompt timely airway rescue and reduce the morbidity and mortality rates associated with undetected respiratory compromise and/or failure. Such a tool would also provide valuable insight into the pathophysiology of sudden infant death syndrome ("SIDS"), or about which babies should receive earlier surgical intervention due to greatest respiratory failure risk such as seen in, but not limited to, Pierre Robin Sequence featuring a cleft palate, micrognathia (abnormally small lower jaw), and glossoptosis (airway obstruction caused by backwards displacement of the tongue)

SUMMARY OF THE DISCLOSURE

The present disclosure overcomes the aforementioned drawbacks by providing systems and methods for non-invasively monitoring airflow in a subject's airway using ultrasound.

It is an aspect of the present disclosure to provide a method for monitoring airflow using an ultrasound system. A region-of-interest that includes a tracheal wall, a cricothyroid ligament, or other anatomical region associated with a subject's airway is selected. Doppler ultrasound signals are acquired from the region-of-interest and are provided to a computer system. Baseline signal data are also provided to the computer system. Baseline signal data may be data acquired from the patient. Additionally or alternatively, baseline signal data may be normative data. A parameter of the Doppler ultrasound signals is compared to a similar parameter in baseline signal data using the computer system. The computer system is then used to identify when the parameter of the acquired Doppler ultrasound signals differs from the similar parameter of the baseline signal data by a selected threshold amount. An alarm is provided to a user when the parameter of the acquired Doppler ultrasound signals is identified as differing from the similar parameter of the baseline signal data by the selected threshold amount.

It is another aspect of the present disclosure to provide an airway monitor that includes an ultrasound transducer, an acquisition system, a processor, and an alarm. The ultrasound transducer is adapted to acquire Doppler ultrasound signals from an anatomical region within the subject's airway (e.g., a tracheal wall, a cricothyroid ligament). The acquisition system receives Doppler ultrasound signals from the ultrasound transducer and communicates those Doppler ultrasound signals to the processor. The processor compares the Doppler ultrasound signals to baseline data and identifies when a parameter of the acquired Doppler ultrasound signals differs from a similar parameter of the baseline signal data by a selected threshold amount. The alarm provides an auditory alarm, a visual alarm, or both, when the parameter of the acquired Doppler ultrasound signals is identified as differing from the similar parameter of the baseline signal data by the selected threshold amount.

The foregoing and other aspects and advantages will appear from the following description. In the description, reference is made to the accompanying drawings that form a part hereof, and in which there is shown by way of illustration a preferred embodiment. This embodiment does not necessarily represent the full scope of the invention, however, and reference is made therefore to the claims and herein for interpreting the scope of the invention.

DETAILED DESCRIPTION

Described here are systems and methods for monitoring airflow changes in a subject's airway. This monitoring may be performed before, during, or following a procedure, or may be used as a general patient monitoring tool. For example, the systems and methods of the present disclosure can be used to monitor signs of airway obstruction or respiratory compromise and/or failure during timeframes where patients have ongoing or residual sedation or anesthetics in their system. The systems and methods can also be implemented for quantitatively measuring airflow and related parameters. As one example, the systems and methods of the present disclosure can be used to quantitatively measure respiratory rate in real-time. In addition, the systems and methods described in the present disclosure provide an improved accuracy because they are capable of detecting actual breaths as opposed to attempted breaths, such as in upper airway obstruction when the chest wall continues to make efforts against a closed glottis.

Moreover, the systems and methods described in the present disclosure are capable of detecting changes in airflow patterns, such as turbulent flow and laminar flow. Additionally or alternatively, the systems and methods described in the present disclosure are capable of detecting sound pressure gradient changes at an air-media interface, such as an air-soft tissue interface. In this way, the propagation of sound waves in air can be detected and tracked.

Currently, no device reliably measures airflow directly, continuously, and instantly. Presently available monitors display information for respiratory ventilation via indirect measurements (e.g., via measuring changes in CO2 and O2). These currently available monitors do not provide direct quantitative measurements of airflow and perform inaccurately in spontaneously breathing patients. Moreover the data provided by these currently available monitors is very delayed, and therefore these monitors often cannot timely detect early airway compromise and/or failure.

The systems and methods described here utilize Doppler ultrasound to measure changes in the airway (e.g., tracheal wall, cricothyroid ligament) during inspiration and expiration. Doppler ultrasound is conventionally used to measure blood flow or the flow of other liquids, such as cerebrospinal fluid. It is a discovery of the present disclosure that Doppler ultrasound signals recorded from anatomical regions within the subject's airway (e.g., the tracheal wall, cricothyroid ligament) can be used to monitor airflow, changes in pressure, or both. By comparing properties of this Doppler signal to a baseline signal, which may include normative data, respiratory compromise and/or failure (e.g., airflow obstruction) can be identified. As an example, respiratory compromise and/or failure can be identified as a percent decrease in Doppler signal amplitude, or as changes in Doppler power spectrum, relative to the baseline signal, or relative to the expected Doppler signal amplitude or power spectrum based on normative data. The systems and methods described in the present disclosure thus provide a direct, real-time measurement of airflow that can be monitored to detect respiratory compromise and/or failure, such as airway obstruction.

During anesthesia, especially in pediatric anesthesia, the systems and methods described in the present disclosure can provide an accurate monitor for airway obstruction and early respiratory comprise, and/or failure leading to more timely intervention and reduced patient morbidity and mortality. The systems and methods described in the present disclosure can also provide an efficient teaching tool in the training of residents and fellows. For example, the measured values from this non-invasive monitor can be more tangibly correlated with clinical changes of the patient, which currently is not possible. Learning these clinical skills for the pediatric population otherwise requires many years of pediatric anesthesia practice. A teaching tool that can expedite this learning process would be advantageous.

The ultrasound-based monitor described in the present disclosure provides a method for detecting alterations in airflow using Doppler signaling within the subject's airway (e.g., along the tracheal wall, cricothyroid ligament). In some embodiments, pulsed wave Doppler techniques can be implemented. In some other embodiments, continuous wave Doppler techniques can be implemented. The non-invasiveness and continuous and instant collection of data makes this tool advantageous for collecting and displaying information about the changing dynamics of airflow in real-time. The systems and methods described in the present disclosure can therefore improve clinical judgment, practice, and teaching.

Figure 1:
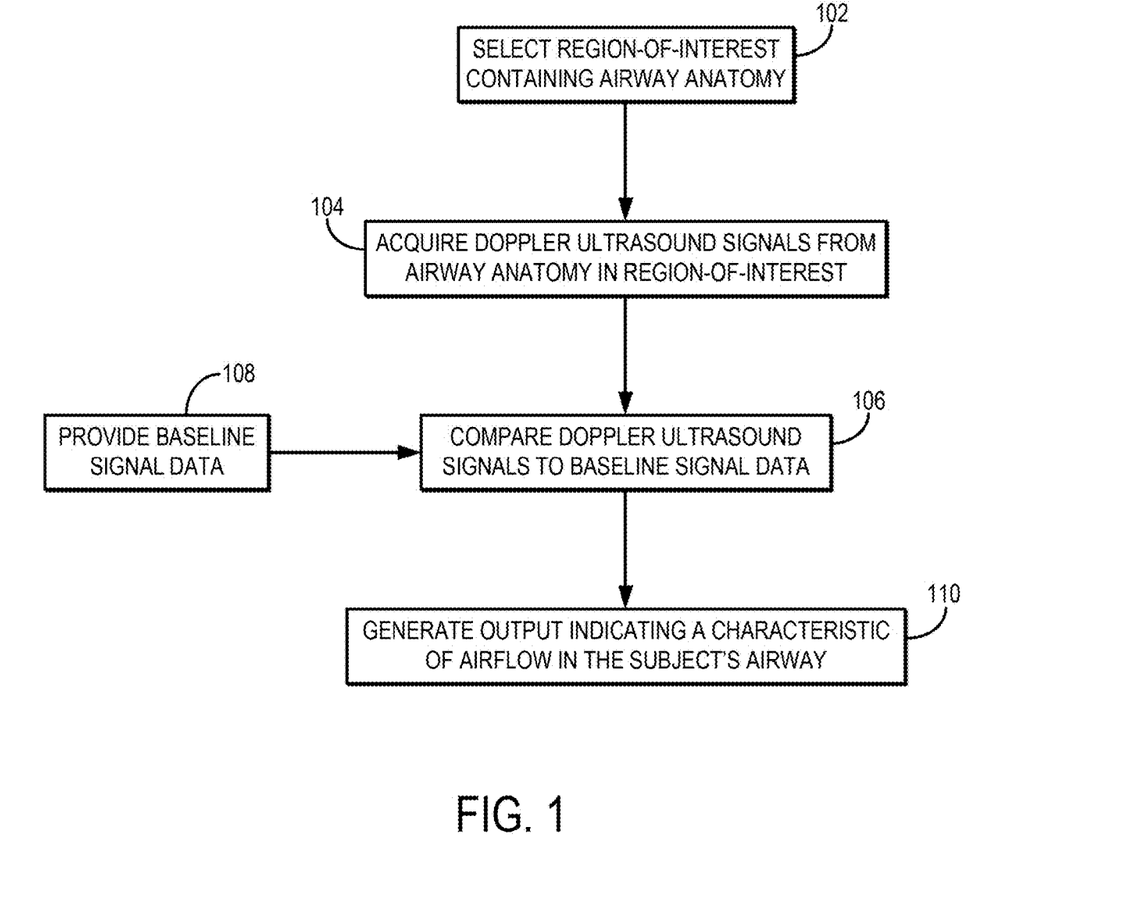
FIG. 1 is a flowchart setting forth the steps of an example method for monitoring for airflow changes by measuring Doppler ultrasound signals from a patient's airway (e.g., tracheal wall, cricothyroid ligament).

Referring now to FIG. 1, a flowchart is illustrated as setting forth the steps of an example method for monitoring a subject for respiratory compromise and/or failure using ultrasound. The method includes selecting a region-of-interest ("ROI") containing an anatomical region in the subject's airway (e.g., the subject's trachea, cricothyroid ligament, other connective or cartilaginous tissue in the trachea, larynx or pharynx), as indicated at step 102. For example, the ROI can be selected by operating the ultrasound system to acquire B-mode images of the subject and identifying an ROI in those B-mode images that includes the desired anatomical region (e.g., the subject's trachea, cricothyroid ligament). In some instances, the ROI can be selected manually. In some other instances, the ROI can be selected on an automatic or semi-automatic basis based on the nature of how the anatomical region is depicted in a B-mode image. For example, the tracheal wall and cricothyroid ligament are hyperechoic in B-mode images and automated or semi-automated selection or segmentation technique can be implemented based on this hyperechoic nature. In still other instances, the ROI can be selected using a machine learning algorithm. For example, a suitable machine learning algorithm can be trained to detect ROIs such that when B-mode images or other ultrasound data are input to the trained machine learning algorithm, an ROI is generated or otherwise selected. As one example, the machine learning algorithm may include a convolutional neural network that has been trained to identify ROIs containing particular anatomical targets such as those discussed in the present disclosure.

Doppler ultrasound signals are then acquired from the ROI using the ultrasound system, as indicated at step 104. Additionally, ultrasound imaging data can also be acquired during this time. Preferably, the Doppler ultrasound signals and imaging data are acquired while the ultrasound transducer is oriented such that the anatomical region (e.g., the tracheal wall, cricothyroid ligament) is being imaged in the longitudinal plane. In other instances, the anatomical region can be imaged in other planes, such as the transverse plane or an oblique plane. The Doppler ultrasound signals, which include velocity data, and ultrasound imaging data are preferably continuously recorded while being analyzed to monitor for airway obstruction or respiratory compromise and/or failure. In some embodiments, power Doppler imaging can be used, in which case the Doppler ultrasound signals may also, or alternatively, include amplitude data (e.g., the total strength of the measured Doppler shift).

As one example, pulsed wave Doppler ultrasound can be used to detect airflow changes across the anatomical region (e.g., trachea, larynx, pharynx); however, continuous wave Doppler can also be used. It is a discovery of the present disclosure that velocities, power spectrum, or both, along the anatomical region within the subject's airway (e.g., tracheal wall, cricothyroid ligament) measured using pulsed wave Doppler correspond to airflow changes, air pressure changes, sound pressure changes, or combinations thereof, in spontaneously breathing and non-intubated patients. Thus, measured changes in the velocities along the anatomical region (e.g., tracheal wall, cricothyroid ligament) can be associated with airflow changes, including airway obstruction or respiratory compromise and/or failure. It is another discovery of the present disclosure that the amplitude of the power Doppler signals measured using power Doppler imaging along the anatomical region (e.g., tracheal wall, cricothyroid ligament) can also be associated with airflow changes, air pressure changes, sound pressure changes, or combination thereof, including airway obstruction or respiratory compromise and/or failure.

In one non-limiting example, the anatomical region (e.g., tracheal wall, cricothyroid ligament) can be imaged in the longitudinal plane using high-resolution ultrasound transducer (e.g., a 10-15 MHz transducer). Pulsed wave Doppler data obtained from the anatomical region in the subject's airway can be used to quantify tissue movement along the anatomical region during the different phases of ventilation. It is a discovery of the present disclosure that increased pulse wave tissue Doppler velocities, power spectrum, or both, can be measured during inspiration and expiration, with the mean values changing with differences in airflow.

In some examples, Doppler ultrasound signals are continuously recorded from the ROI while the subject is breathing under anesthesia, sedation, or both. During breathing, changes in airflow in the airway will be recorded as changes in the measured Doppler ultrasound signals, which can be compared to baseline data that were acquired before the subject was placed under anesthesia, sedation, or both. As mentioned above, in some instances the baseline signal data may include normative data. A suitable correlation or other algorithm can be used to identify critical changes in the subject's airflow, relative to the baseline data, in real-time, as described below.

In some other examples, the Doppler ultrasound signals can be compared to normative data in addition to, or in alternative to, baseline data. Such normative data may include data associated with expected normal airflow in a healthy patient, such as expected normal airflow velocities in a healthy patient. As one example, this normative data can be provided from a database of measured, normal airflow, which may have been reported in previous clinical or scientific studies. In examples where the Doppler ultrasound signals are compared to normative data, the suitable correlation or other algorithm can be used to identify critical changes in the subject's airflow relative to the normative data. By comparing the Doppler ultrasound signals to normative data, it is contemplated that additional information about the patient can be provided to the clinician.

For example, if comparing the Doppler ultrasound signals to normative data indicates a significant deviation from the normative data, this deviation can be quantified or qualified and presented to the clinician. Such deviations provide information to a clinician that may indicate an underlying respiratory issues, such as an undiagnosed restrictive airway disease, or the like.

As another example, in the emergency room setting, comparing the Doppler ultrasound signals to normative data can also provide information to a clinician that may indicate whether the patient is in respiratory distress. This information may help inform a clinician whether to administer emergent sedation in preparation for intubation (e.g., placing an endotracheal breathing tube) to provide respiratory support, or may help a clinician monitor treatment provided to a patient (e.g., whether a patient has an allergic response to a treatment).

It is noted that while Doppler ultrasound signals are being acquired, additional physiological data can also be measured. For example, electrocardiograms can be recorded using ECG leads to monitor respiratory impedance and respiratory phases. Although these additional physiological data are not necessary to monitor airflow or to detect airway obstruction or respiratory compromise and/or failure, they can supplement the ultrasound-based data and provide additional information to be relied upon.

Thus, the Doppler ultrasound signals are compared to baseline signal data, as indicated at step 106. Baseline signal data can be provided to the ultrasound system or to a computer system in communication with the ultrasound system for this comparison, as indicated at step 108. For example, the baseline signal data can be Doppler ultrasound signals acquired from the patient before the patient undergoes a medical procedure. That is, the baseline signal data can be acquired before the patient is administered an anesthetic agent. In some instances, the baseline signal data can include model, or normative, data corresponding to expected normal respiration for a particular patient population group, which may include Doppler ultrasound signals acquired from a different patient or subject (e.g., an age-matched, gender-matched patient). In other examples, the baseline signal data can include previously acquired portions of the Doppler ultrasound signals acquired in step 104. For instance, in a real-time monitoring application the most currently acquired Doppler ultrasound signals can be compared to Doppler ultrasound signals acquired in previous time points. As one example, a sliding window analysis could be performed, in which Doppler ultrasound signals acquired within a current time window are compared with Doppler ultrasound signals acquired outside of (i.e., prior to) the time window. In these instances, cumulative changes, or a series of changes, in the parameters of the Doppler ultrasound signals can be monitored, such that a trending change in the parameters can be identified.

As one example, the peak height of the Doppler ultrasound signals during different respiratory phases can be compared with the baseline signal data. For instance, the peak heights at inspiration, expiration, or both can be compared with baseline. In some implementations, the Doppler ultrasound signals can be Doppler spectra that indicate a velocity associated with the underlying airflow. In these instances, the height of the Doppler ultrasound signals will correspond to airflow velocities. In some other implementations, the Doppler ultrasound signals can be power Doppler signals that indicate the total strength, or amplitude, of the frequency shifts associated with the underlying airflow. In these instances, the height of the Doppler ultrasound signals will correspond to the strength of the Doppler signals caused by airflow.

As will be described below, comparing the Doppler ultrasound signals with the baseline signal data can generally result in generating an output that indicates a characteristic of airflow in the subject's airway, as indicated at step 110. The characteristic of airflow in the subject's airway may include or otherwise indicate airflow changes, air pressure changes, sound pressure changes, or combinations thereof. For example, the characteristic of airflow may include velocity; airflow pattern (e.g., turbulent versus laminar flow); a quantification of turbulence; acceleration of flow; deceleration of flow; air pressure fluctuations; sound pressure gradient changes at an air-media interface; or combinations thereof. In some instances, this includes generating the output as an alarm to the user, such as when a threshold change is detected. In other instances, this includes generating the output as an indication of a quantification or characterization of the airflow. As one example, the output may include images or other visual indications that are displayed to a user, such as via graphical user interface. Such images or visual indications can be overlaid with or displayed alongside images generated from the Doppler ultrasound signals, or with other images obtained with the ultrasound system (e.g., B-mode images).

As another example, the Doppler ultrasound signals can be correlated with the baseline signal data, and portions of the Doppler ultrasound signals that correlate with the baseline signal data can be compared. As above, when changes in the correlated portions of the Doppler ultrasound signals and the baseline signal data exceed a threshold, an alarm can be provided to a user.

It is contemplated that a threshold change in the range of 20-40 percent relative to the baseline signal data can be associated with early airway compromise and/or failure and, thus, can be relied upon to trigger an alarm. When using the real-time Doppler ultrasound signals as the baseline data, as described above, a lower threshold for triggering an alarm may be used since subtle or trending changes in the parameters of the Doppler ultrasound signals may be more difficult to discern than when comparing the Doppler ultrasound signals to previously acquired or normative data. A lower threshold can also be used as desired depending on the perceived risk for the particular patient. For instance, a lower threshold (e.g., 10-30 percent) may be desirable in patients with higher risk for airway obstruction or respiratory compromise and/or failure.

In some instances, comparing the Doppler ultrasound signals to baseline signal data at step 106 can include inputting the Doppler ultrasound signals to a deep learning model, or other suitable machine learning algorithm, that was trained with baseline signal data. For example, a deep learning model, supervised machine learning algorithm, or other suitable machine learning algorithm, can be trained on baseline signal data to predict, classify, or otherwise detect different breathing patterns based on acquired Doppler ultrasound signals. The machine learning algorithms can also be trained to compute flow parameters from the Doppler ultrasound signals.

The trained machine learning algorithm can include or otherwise implement a support vector machine ("SVM"), a random forest, a conditional random field, a hidden Markov model, a neural network, and other deep learning models or algorithms.

In some instances, a machine learning algorithm can be trained on baseline signal data that has been annotated or otherwise labeled. For example, baseline signal data can be annotated or otherwise labeled to identify different breathing patterns, including normal, fast, shallow, deep, slow, Valsalva, and so on.

Comparing the Doppler ultrasound signals to the baseline signal data in step 106 may also include generating an output that characterizes the airflow in the subject's airway. For instance, comparing the Doppler ultrasound signals to baseline signal data may identify airflow as turbulent or laminar airflow. This information can be reported to the clinician, such as by generating a display that may form a part of a graphical user interface. As noted, the comparison of the Doppler ultrasound signals with the baseline data may include inputting the Doppler ultrasound signals to a machine learning algorithm that has been trained on the baseline signal data. In these instances, the machine learning algorithm can generate output that characterizes the airflow in the subject's airway. As one example, the trained machine learning algorithm can generate output as annotated Doppler ultrasound signals, which are labeled with a characterization of the airflow being turbulent or laminar.

In addition to characterizing whether airflow is turbulent or laminar, the degree of turbulence can be determined and reported. For instance, comparing the Doppler ultrasound signals to the baseline signal data can include generating output that quantifies or otherwise characterizes the degree of turbulent airflow, such as the degree of turbulence at an air-wall interface of the subject's airway. As described above, the comparison of the Doppler ultrasound signals with the baseline data may include inputting the Doppler ultrasound signals to a machine learning algorithm that has been trained on the baseline signal data. In these instances, the machine learning algorithm can generate output that characterizes or otherwise quantifies the degree of turbulence.

In some other instances, the degree of turbulence can be determined or otherwise characterized using a waveform analysis of the Doppler ultrasound signals. For instance, the strength, shape, and pattern of waveforms in the Doppler ultrasound signals can be used to quantify or otherwise characterize the degree of turbulence in the Doppler ultrasound signals.

In still other instances, other parameters of airflow can be quantified or characterized by comparing the Doppler ultrasound signals to baseline signal data, which as noted may include training a suitable machine learning algorithm on the baseline signal data. As one non-limiting example, multivariate linear regression ("MVR") and random forest ("RF") regression can be applied to predict the flow magnitude of inspiration and expiration. Predicting flow values can aid in the detection of early obstruction and can also provide additional data about the information content of the ultrasound signal in respect to flow.

Figure 2A:
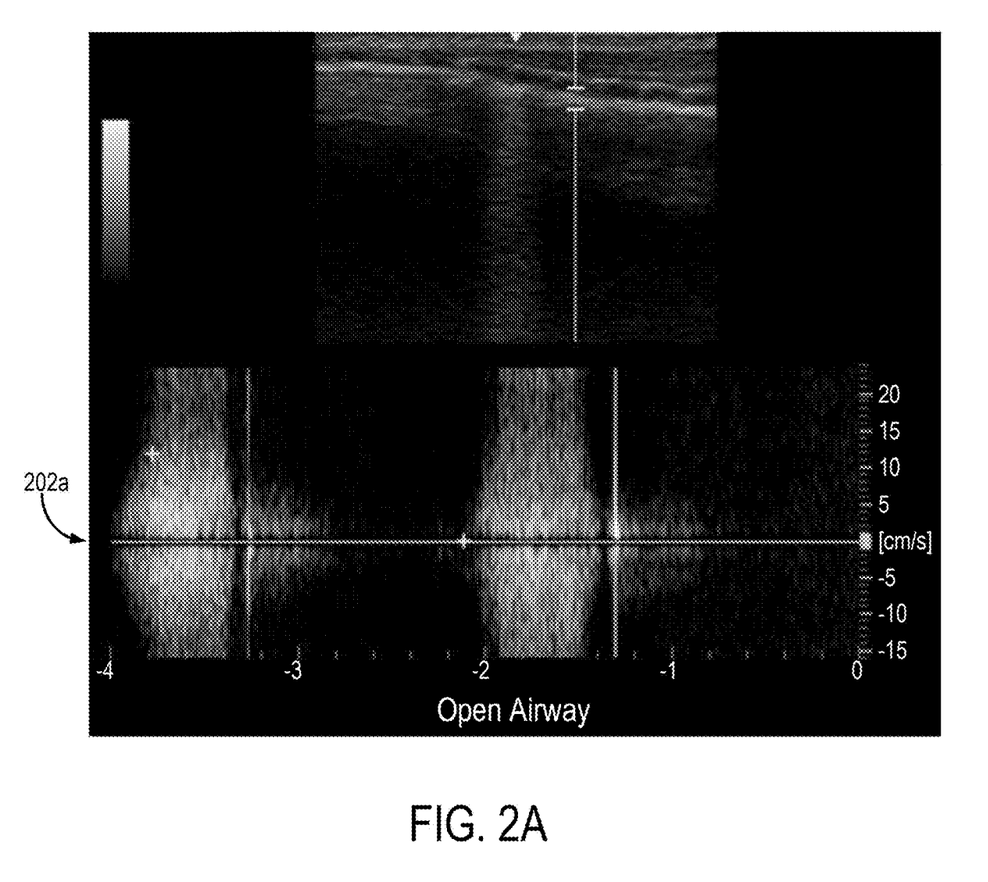
FIGS. 2A, 2B, and 2C are examples of Doppler ultrasound signals showing changes in peak amplitude and peak width in measurements from a tracheal wall, where these changes are associated with changes in airflow.
Figure 2B:
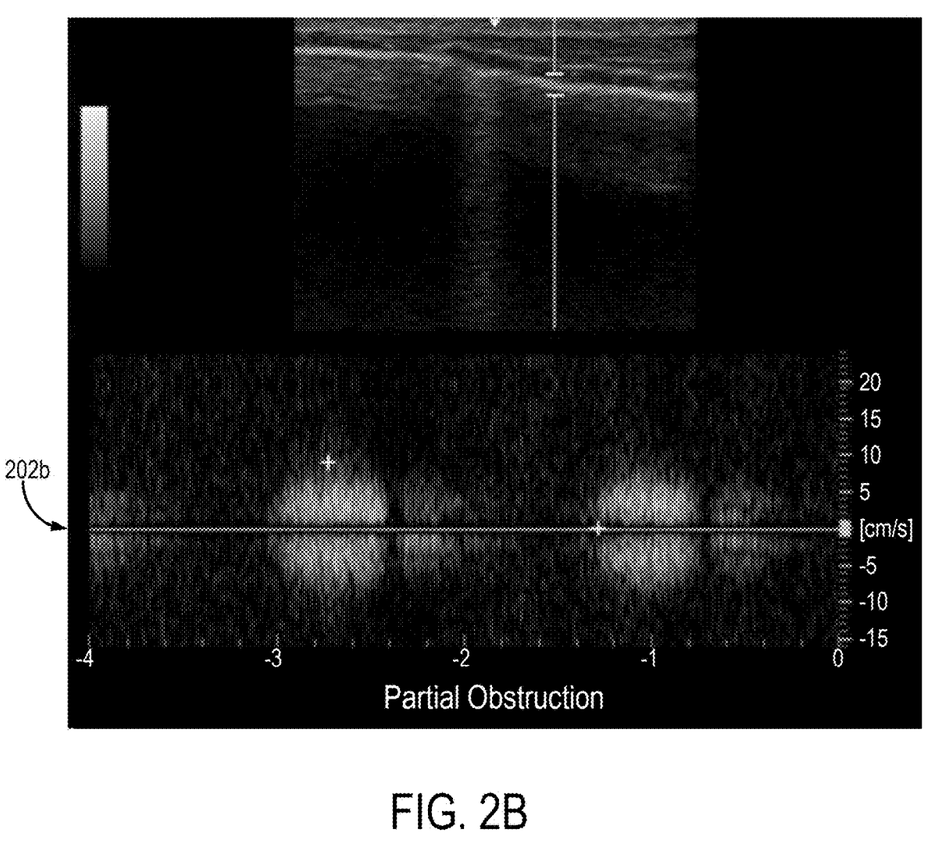
Figure 2C:
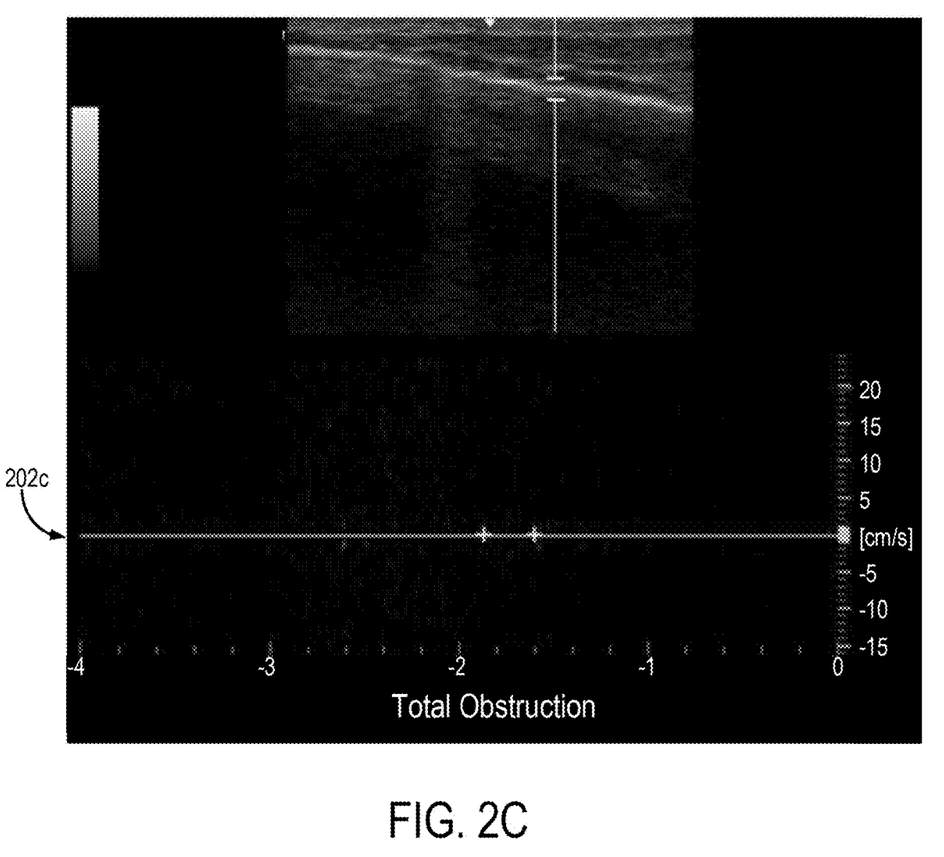

FIGS. 2A, 2B, and 2C are examples of Doppler ultrasound signals showing changes in peak amplitude and peak width measured at the tracheal wall and associated with changes in airflow. The images obtained in FIGS. 2A-2C were acquired using pulsed wave Doppler during the respiratory cycle with varying amounts of obstruction. In this experimental study, airway obstruction was mimicked using a catheter with a balloon tip that was advanced into the distal trachea of euthanized dogs via an indwelling endotracheal tube. The balloon was insufflated using predetermined volumes to create various degrees of obstruction. As seen in FIGS. 2A-2C, a progressive dampening of the Doppler ultrasound signal was observed with each gradation of airway obstruction, with total loss of signal with complete obstruction of the airway.

In these examples, the Doppler ultrasound signals include Doppler spectra 202*a*, 202*b*, 202*c* indicating frequency shifts related to the velocity associated with the underlying airflow. In the case of FIGS. 2A and 2B, the Doppler spectra 202*a* and 202*b*, respectively, indicate that a decrease in airflow is observable as a corresponding decrease in the Doppler spectra, such as a decrease in the amplitude of the Doppler spectra. In the case of FIG. 2C, the Doppler spectrum 202*c* indicates that there is no measured airflow as a result of the complete obstruction of the airway.

Figure 3A:
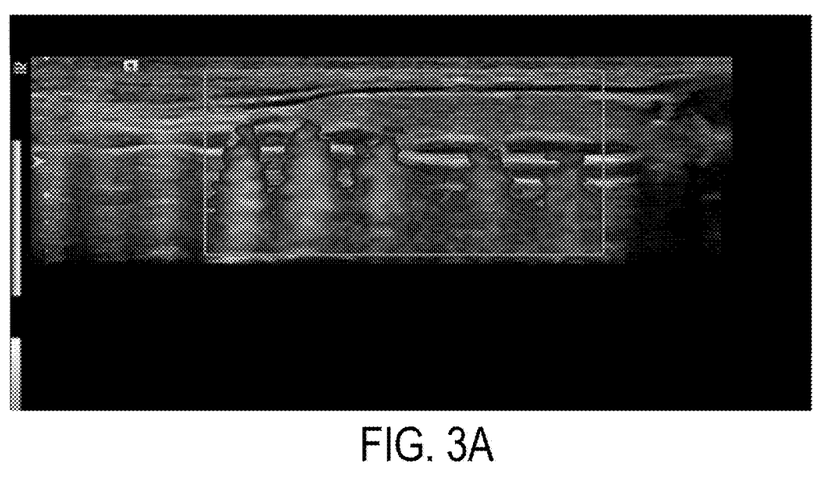
FIGS. 3A, 3B, and 3C are example of power Doppler ultrasound signals showing changes in the total strength of Doppler signal measurements from a tracheal wall, where these changes are associated with changes in airflow.
Figure 3B:
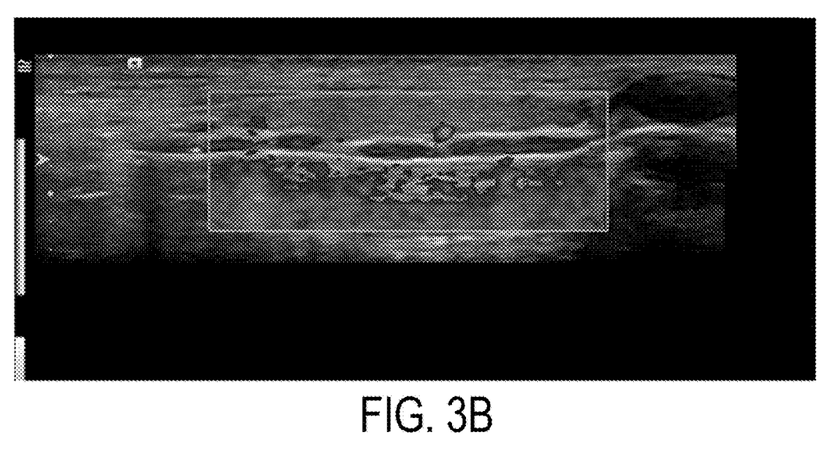
Figure 3C:
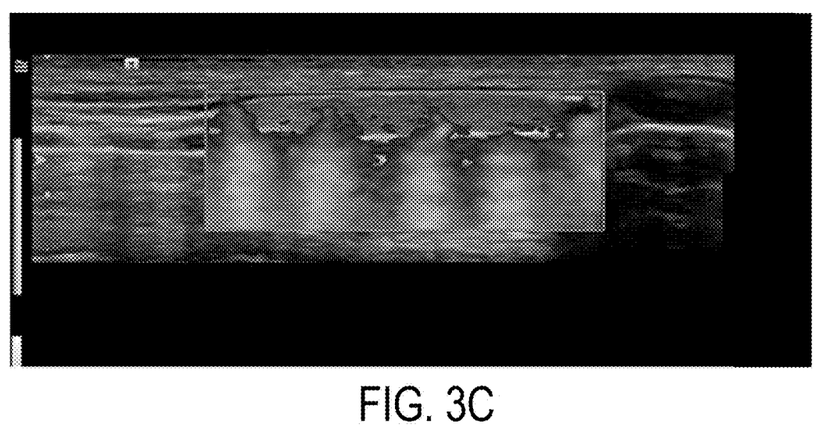

FIGS. 3A, 3B, and 3C are examples of Doppler ultrasound signals acquired with power Doppler imaging and showing changes in peak amplitude and peak width measured at the tracheal wall and associated with changes in airflow.

In addition to monitoring changes in peak heights of the Doppler ultrasound signals at one or more points during the respiratory phase, other parameters of the Doppler ultrasound signals can be measured, monitored, and compared. For example, the width of the Doppler ultrasound peaks at one or more points during the respiratory phase can be measured, monitored, and compared with similar measures in the baseline signal data.

As another example, the time between Doppler ultrasound peaks can be measured to quantify the subject's respiratory rate. By quantifying the subject's respiratory rate while also monitoring changes in the subject's airflow, the quality of each breath taken by the subject can be evaluated. For example, the number of breaths in a given time period can be quantified, while also monitoring the volume (e.g., a deep breath with good airflow versus a shallow breath with low airflow) of airflow in each breath. This information can be presented to the user in real-time to provide an additional patient monitoring tool.

As mentioned above, a determination is made while Doppler ultrasound signals are being recorded whether the comparison of the Doppler ultrasound signals with the baseline signal data satisfies one or more preselected conditions or criteria. When a condition or criteria is met (e.g., a threshold change is detected), an alarm can be provided to the user. In some instances, different alarms can be provided based on different criteria. For example, a first alarm can be provided when a first threshold is met and a second alarm can be provided when a second threshold is met. The first alarm can correspond to early airway compromise and/or failure, and the second alarm can correspond to complete airway obstruction. Thus, varying levels of feedback can be provided about airway obstruction or other respiratory compromise and/or failure.

Figure 4:
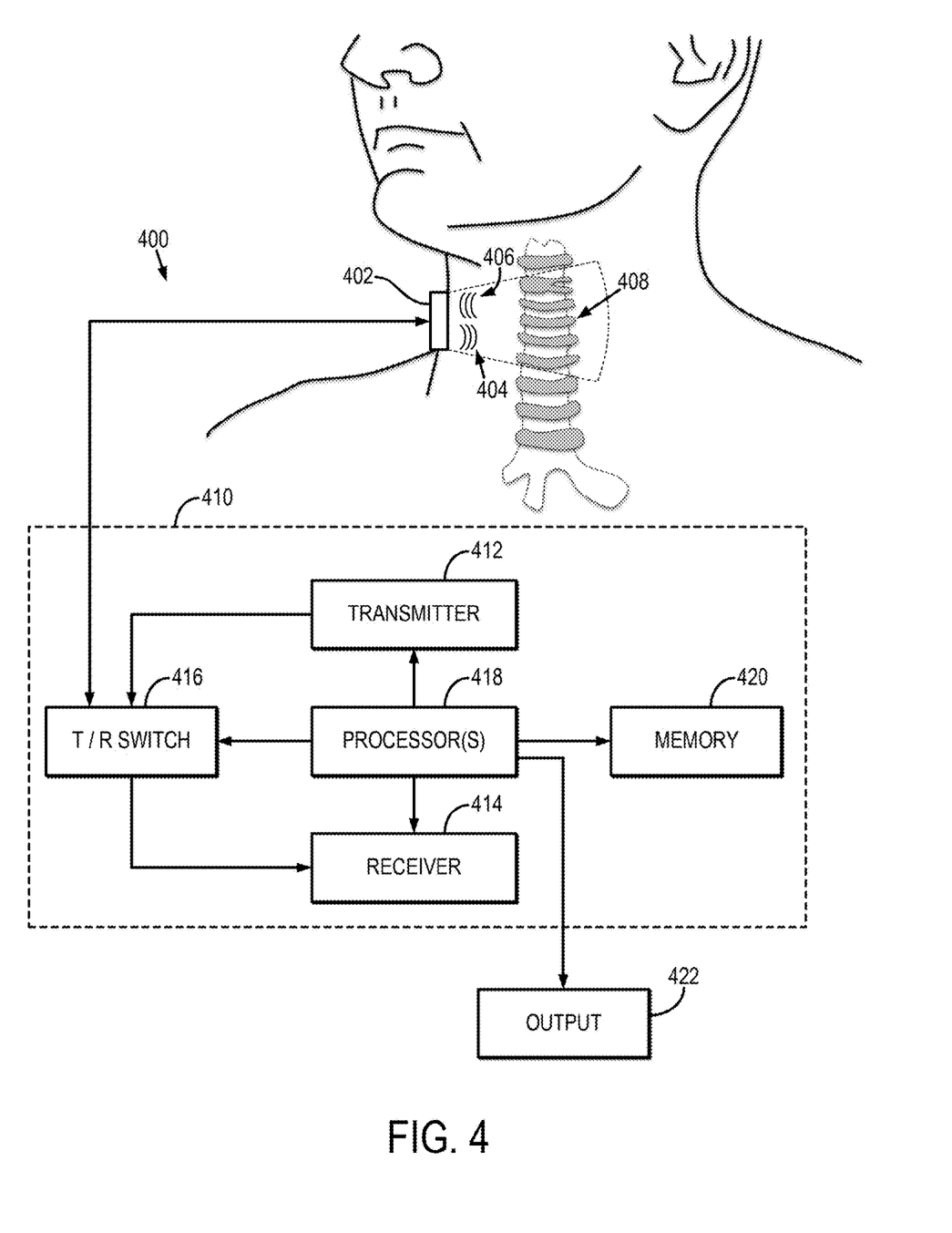
FIG. 4 is a block diagram of an example ultrasound-based airway monitor that can implement the methods described here, and can similarly be adapted for continuous monitoring of a patient's airway (e.g., tracheal wall, cricothyroid ligament).

FIG. 4 illustrates the main components of an example airway monitor 400 that can implement the methods described here. In general, the airway monitor 400 can implement an ultrasound system that includes an ultrasound transducer 402 that transmits ultrasonic waves 404 and receives ultrasonic echoes 406 from an anatomical region 408 of a patient, which may be a tracheal wall, a cricothyroid ligament, or other suitable connective or cartilaginous tissue in the trachea, larynx, or pharynx. The ultrasound transducer 402 is generally controlled by a controller 410.

The ultrasound transducer 402 can include a plurality of separately driven transducer elements, and can include any suitable ultrasound transducer array, including linear arrays, curved arrays, phased arrays, and so on. Similarly, the ultrasound transducer 402 can include a 1 D transducer, a 1.5 D transducer, a 1.75 D transducer, a 2 D transducer, a 3 D transducer, and so on.

When energized by a transmitter 412, the ultrasound transducer 402 produces a burst of ultrasonic energy (e.g., ultrasonic waves 404). The ultrasonic energy reflected back to the ultrasound transducer 402 (e.g., an echo, or ultrasonic waves 406) from the tracheal wall 408 is converted to an electrical signal (e.g., an echo signal) by the ultrasound transducer 402 and can be applied separately to a receiver 414 through a set of switches 416. The transmitter 412, receiver 414, and switches 416 are operated under the control of one or more processors 418. The transmitter 412, receiver 414, and switches 416 can be collectively referred to as an acquisition system.

In some instances, the ultrasound transducer 402 can be configured to be positioned or otherwise arranged on the subject's neck, allow for hands-free operation of the airway monitor 400 during a procedure. As one example, the ultrasound transducer 402 can be made to be coupled to the subject's skin surface, such as using an adhesive, a strap, or the like. As another example, the transducer 402 may be composed of piezoelectric crystals or capacitive micromachined ultrasonic transducers ("CMUT") that are embedded into a gelatinous media that adheres to the subject's skin. Such a transducer 402 can communicate via a wireless or wired connection.

The transmitter 412 can be programmed to transmit ultrasound waves for continuous wave Doppler imaging, pulsed wave Doppler imaging, or both. The receiver 414 can be programmed to implement a suitable detection sequence for the measuring Doppler shifts caused by airflow in the subject's airway and, thus, for acquiring Doppler ultrasound signals.

In some configurations, the transmitter 412 and the receiver 414 can be programmed to implement a high frame rate. For instance, a frame rate associated with an acquisition pulse repetition frequency ("PRF") of at least 100 Hz can be implemented. In some configurations, the airway monitor 400 can sample and store at least one hundred ensembles of echo signals in the temporal direction. The airway monitor 400 can implement a detection sequence that includes one of conventional line-by-line scanning, compounding plane wave imaging, compounding diverging beam imaging, continuous wave Doppler imaging, and pulsed wave Doppler imaging.

A scan can be performed by setting the switches 416 to their transmit position, thereby directing the transmitter 412 to be turned on momentarily to energize the ultrasound transducer 402 to transmit ultrasound waves 404 to the anatomical region 408. The switches 416 can then be set to their receive position and the subsequent echo signals produced by the ultrasound transducer 402 in response to one or more detected echoes (e.g., ultrasound waves 406) are measured and applied to the receiver 414. The separate echo signals from the transducer elements in the ultrasound transducer 402 can be combined in the receiver 414 to produce a single echo signal.

The echo signals (e.g., Doppler ultrasound signals) are communicated to one or more processors 418 to process Doppler ultrasound signals or images generated from such signals. As an example, the one or more processor 418 can process the Doppler ultrasound signals to can be programmed to implement the methods described in the present disclosure for generating images that depict the anatomical region 408 of the patient, for measuring parameters of Doppler ultrasound signals recorded from the anatomical region 408 of the patient, and for comparing those parameters with similar parameters from baseline signal data provided to the one or more processors 418. In some implementations, the one or more processors 418 can perform power Doppler analyses, such as by generating power Doppler signals (e.g., total strength or amplitude of the measured Doppler signals) from the acquired ultrasound signals. The one or more processors 418 can be in communication with a memory 420 that contains the baseline data described above, and which can store Doppler ultrasound signals acquired by the airway monitor 400 and other suitable data.

The output from the one or more processors 418 can be provided to an output 422, which can include a display, speaker, or both. For instance, the output 422 can include an alarm, which may be a display for generating a visual alarm, or a speaker for generating an auditory alarm. In some examples, images produced from the Doppler ultrasound signals by the one or more processor 418 can be displayed on an output 422 that includes a display.

Figure 5:
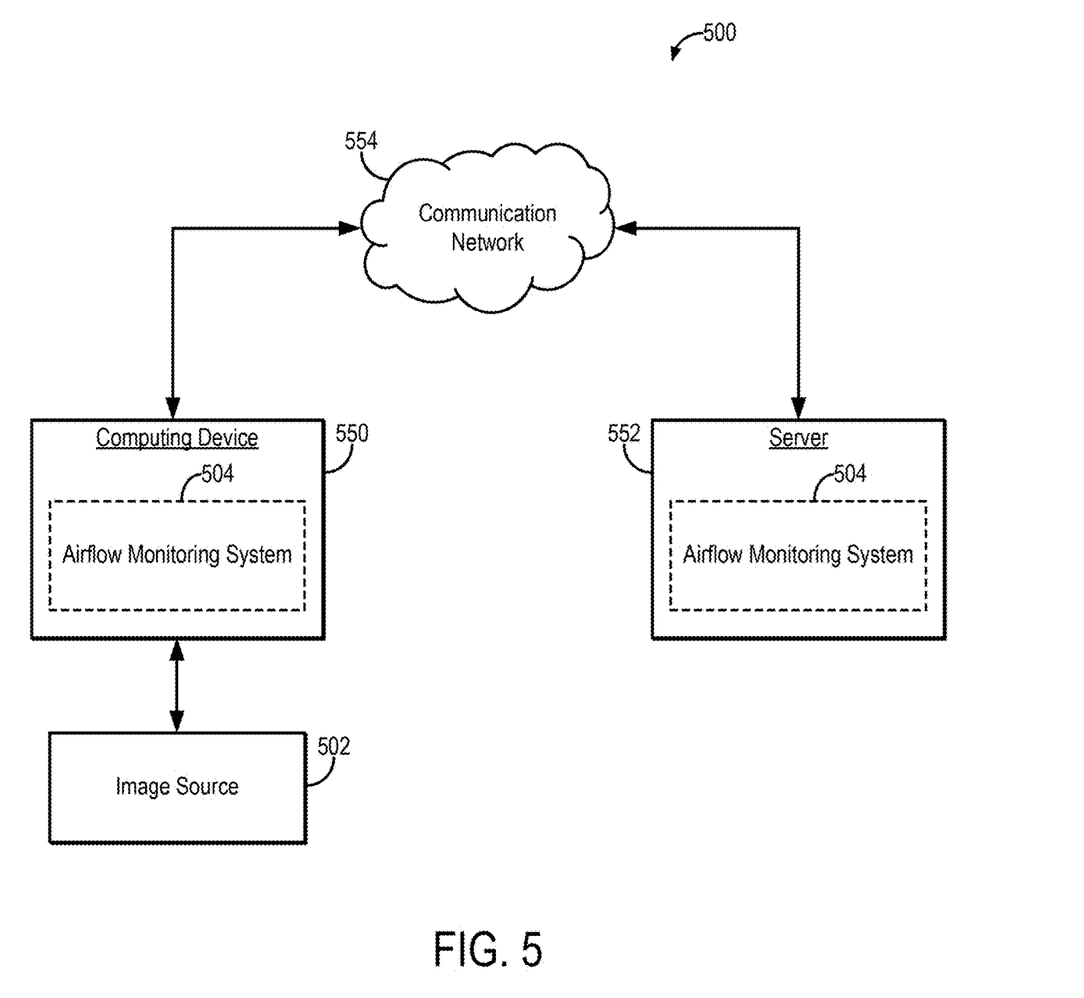
FIG. 5 is a block diagram of an example system that can implement an airflow monitor as described in the present disclosure.

Referring now to FIG. 5, an example of a system 500 for monitoring airflow in a subject in accordance with some embodiments of the systems and methods described in the present disclosure is shown. As shown in FIG. 5, a computing device 550 can receive one or more types of data (e.g., Doppler ultrasound signal data) from image source 502, which may be an ultrasound image source. In some embodiments, computing device 550 can execute at least a portion of an airflow monitoring system 504 to monitor airflow in a subject's airway from data received from the image source 502.

Additionally or alternatively, in some embodiments, the computing device 550 can communicate information about data received from the image source 502 to a server 552 over a communication network 554, which can execute at least a portion of the airflow monitoring system 504 to monitor airflow in a subject's airway from data received from the image source 502. In such embodiments, the server 552 can return information to the computing device 550 (and/or any other suitable computing device) indicative of an output of the airflow monitoring system 504 to monitor airflow in a subject's airway from data received from the image source 502.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also reconstruct images from the data.

In some embodiments, image source 502 can be any suitable source of image data (e.g., measurement data, images reconstructed from measurement data), such as an ultrasound system, another computing device (e.g., a server storing image data), and so on. In some embodiments, image source 502 can be local to computing device 550. For example, image source 502 can be incorporated with computing device 550 (e.g., computing device 550 can be configured as part of a device for capturing, scanning, and/or storing images). As another example, image source 502 can be connected to computing device 550 by a cable, a direct wireless link, and so on. Additionally or alternatively, in some embodiments, image source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a satellite communications network (e.g., SATCOM), a radio communications network, a wired network, and so on. In some embodiments, communication network 554 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
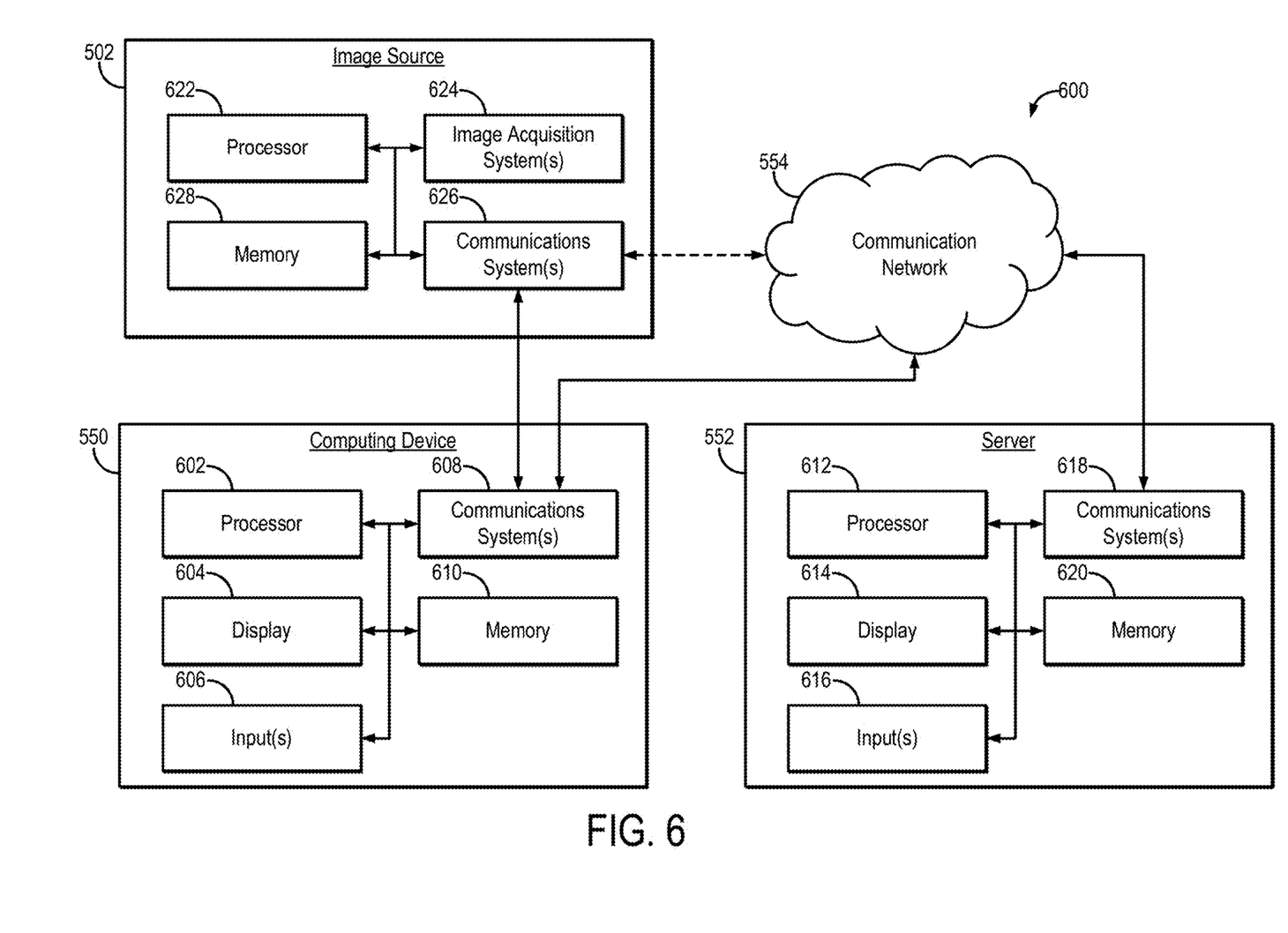
FIG. 6 is a block diagram of example hardware components that can be used to implement the system of FIG. 5.

Referring now to FIG. 6, an example of hardware 600 that can be used to implement image source 502, computing device 550, and server 552 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, image source 502 can include a processor 622, one or more image acquisition systems 624, one or more communications systems 626, and/or memory 628. In some embodiments, processor 622 can be any suitable hardware processor or combination of processors, such as a CPU, a GPU, and so on. In some embodiments, the one or more image acquisition systems 624 are generally configured to acquire data, images, or both, and can include an ultrasound transducer. Additionally or alternatively, in some embodiments, one or more image acquisition systems 624 can include any suitable hardware, firmware, and/or software for coupling to and/or controlling operations of an ultrasound transducer. In some embodiments, one or more portions of the one or more image acquisition systems 624 can be removable and/or replaceable.

Note that, although not shown, image source 502 can include any suitable inputs and/or outputs. For example, image source 502 can include input devices and/or sensors that can be used to receive user input, such as a keyboard, a mouse, a touchscreen, a microphone, a trackpad, a trackball, and so on. As another example, image source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more image acquisition systems 624, and/or receive data from the one or more image acquisition systems 624; to images from data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of image source 502. In such embodiments, processor 622 can execute at least a portion of the program to generate images, transmit information and/or content (e.g., data, images) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present invention has been described in terms of one or more preferred embodiments, and it should be appreciated that many equivalents, alternatives, variations, and modifications, aside from those expressly stated, are possible and within the scope of the invention.

The invention claimed is:

1. A computerized method for analyzing ultrasound signals, the method comprising:
   (a) selecting a region-of-interest in a subject that includes an anatomical region that includes connective tissue corresponding to the subject's airway, wherein the anatomical region includes in at least one of a trachea, larynx, or pharynx of the subject;
   (b) acquiring Doppler ultrasound signals from the connective tissue in the region-of-interest using an ultrasound system and providing the Doppler ultrasound signals to a computer system;
   (c) comparing the Doppler ultrasound signals acquired from the connective tissue to baseline signal data using the computer system, generating output that indicates a characteristic of airflow in the subject's airway; and
   (d) providing the output to a user with the computer system, wherein the output indicates a change in airflow in the subject's airway as measured by the characteristic of airflow generated from the Doppler ultrasound signals acquired from the connective tissue.

2. The method of claim 1, wherein comparing the Doppler ultrasound signals to the baseline signal data comprises comparing a parameter of the Doppler ultrasound signals with a parameter of the baseline signal data.

3. The method of claim 2, wherein generating the output comprises identifying with the computer system when the parameter of the acquired Doppler ultrasound signals differs from the parameter of the baseline signal data by a selected threshold amount.

4. The method as recited in claim 2, wherein the output generated in step (c) characterizes the airflow in the subject's airway as one of turbulent or laminar.

5. The method as recited in claim 2, wherein the output generated in step (c) quantifies a degree of turbulence of the airflow in the subject's airway.

6. The method as recited in claim 2, wherein the output generated in step (c) quantifies the airflow in the subject's airway.

7. The method as recited in claim 2, wherein providing the output to the user comprises generating an alarm when the parameter of the acquired Doppler ultrasound signals is identified as differing from the parameter of the baseline signal data by the selected threshold amount.

8. The method as recited in claim 7, wherein the parameter of the acquired Doppler ultrasound signals is an amplitude of the Doppler ultrasound signals at a particular respiratory phase and the parameter of the baseline signal data is an amplitude of the baseline signal data at the particular respiratory phase.

9. The method as recited in claim 7, wherein the parameter of the acquired Doppler ultrasound signals is a peak width of the Doppler ultrasound signals at a particular respiratory phase and the parameter of the baseline signal data is a peak width of the baseline signal data at the particular respiratory phase.

10. The method as recited in claim 7, wherein the selected threshold is a percent decrease of the parameter relative to the parameter of the baseline signal data.

11. The method as recited in claim 10, wherein the percent decrease is in a range of 20 percent to 40 percent.

12. The method as recited in claim 1, wherein comparing the Doppler ultrasound signals to the baseline signal data comprises inputting the Doppler ultrasound signals to a machine learning algorithm that has been trained on the baseline signal data.

13. The method as recited in claim 1, wherein the connective tissue comprises a cartilaginous tissue.

14. The method as recited in claim 1, wherein the connective tissue comprises a cricothyroid ligament.

15. The method as recited in claim 1, wherein the Doppler ultrasound signals are acquired in a longitudinal plane relative to the connective tissue.

16. The method as recited in claim 1, wherein the Doppler ultrasound signals are acquired in a transverse plane relative to the connective tissue.

17. The method as recited in claim 1, wherein the baseline signal data is baseline Doppler ultrasound signal data acquired from the subject before acquiring the Doppler ultrasound signals in step (a).

18. The method as recited in claim 1, wherein the Doppler ultrasound signals comprise Doppler spectra indicating velocity data associated with airflow in the subject's airway.

19. The method as recited in claim 1, wherein the Doppler ultrasound signals include power Doppler signals indicating amplitude data associated with airflow in the subject's airway.

20. The method as recited in claim 1, wherein the baseline signal data comprise normative data.

21. An airway monitor comprising:
    an ultrasound transducer adapted to receive Doppler ultrasound signals from a region-of-interest containing a cricothyroid ligament of a subject;
    an acquisition system in communication with the ultrasound transducer to receive Doppler ultrasound signals from the ultrasound transducer, wherein the Doppler ultrasound signals are acquired from the cricothyroid ligament of the subject;
    a processor in communication with the acquisition system, wherein the processor receives the Doppler ultrasound signals from the acquisition system and compares the Doppler ultrasound signals acquired from the cricothyroid ligament to baseline data to identify when a parameter of the Doppler ultrasound signals differs from a parameter of the baseline signal data by a selected threshold amount indicating a change in airflow in an airway of the subject as measured by the Doppler ultrasound signals acquired from the cricothyroid ligament of the subject; and
    an alarm in communication with the processor, wherein the alarm provides at least one of an auditory or a visual indication when the parameter of the acquired Doppler ultrasound signals is identified by the processor as differing from the parameter of the baseline signal data by the selected threshold amount.

22. The airway monitor as recited in claim 21, wherein the processor is programmed to compare the Doppler ultrasound signals to the baseline data in order to identify when at least one of an amplitude or a peak width of the Doppler ultrasound signals differs from at least one of an amplitude or peak width of the baseline signal data by a selected threshold amount.

23. The airway monitor as recited in claim 21, wherein the selected threshold is a percent decrease of the parameter relative to the parameter of the baseline signal data.

24. The airway monitor as recited in claim 23, wherein the percent decrease is in a range of 20 percent to 40 percent.

* * * * *